United States Patent [19]

Blytas et al.

[11] Patent Number: 4,696,726

[45] Date of Patent: Sep. 29, 1987

[54] PROCESS FOR THE PRODUCTION OF DICHLOROHYDRIN

[75] Inventors: George C. Blytas; F. N. Grimsby, both of Houston, Tex.; John F. Scamehorn, Norman, Okla.

[73] Assignee: Shell Oil Company, Houston, Tex.

[21] Appl. No.: 885,519

[22] Filed: Jul. 14, 1986

[51] Int. Cl.$^4$ .............................................. B01D 13/02
[52] U.S. Cl. ........................ 204/182.4; 210/195.2; 210/652; 568/847; 568/850
[58] Field of Search ...................... 204/182.4; 568/847, 568/850; 210/652, 195.2

[56] References Cited

U.S. PATENT DOCUMENTS 2,714,121 7/1955 Anderson et al. .................. 568/847

FOREIGN PATENT DOCUMENTS

| 2554732 | 5/1985 | France | 210/652 |
| 1040383 | 4/1976 | Japan | 210/652 |
| 0174736 | 9/1985 | Japan | 210/652 |
| 0639236 | 5/1984 | U.S.S.R. | 568/847 |

*Primary Examiner*—Arthur P. Demers
*Attorney, Agent, or Firm*—Ronald R. Reper

[57] ABSTRACT

A continuous process for the production of dichlorohydrin by the reaction of allyl chloride, water and chlorine having substantially lower energy requirements than conventional processes, wherein the reaction mixture is subjected to reverse osmosis to concentrate the dichlorohydrin and to provide a permeate stream substantially free of dichlorohydrin, which permeate stream is recycled to the reaction.

5 Claims, 1 Drawing Figure

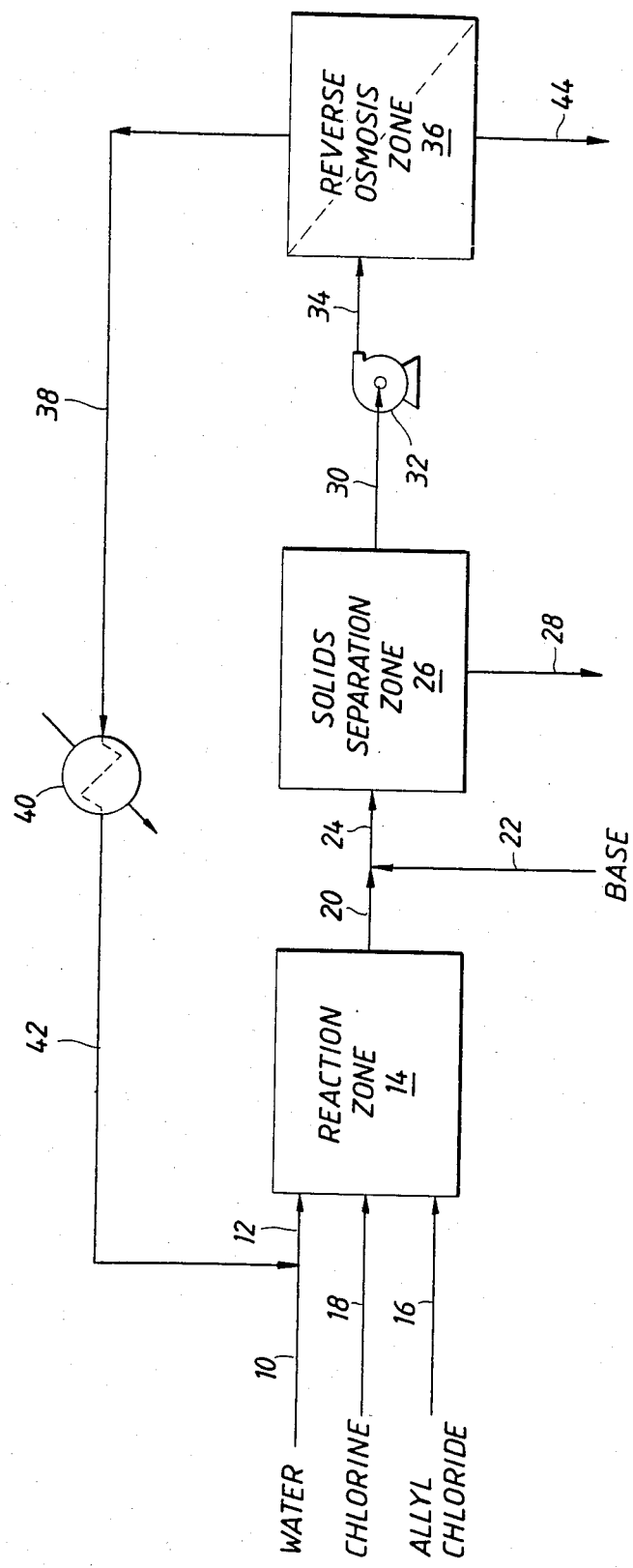

4,696,726

PROCESS FOR THE PRODUCTION OF DICHLOROHYDRIN

BACKGROUND OF THE INVENTION

It is known to prepare dichlorohydrin by reacting in a reaction zone allyl chloride, water and chlorine in dilute aqueous phase, see e.g., U.S. Pat. Nos. 2,714,121 and 2,714,123, incorporated herein by reference. The term "dichlorohydrin" herein designates the isomers 2,3 dichloro-1-propanol and 1,3 dichloro-1-propanol. The reaction zone effluent may be worked up in different ways to recover the dichlorohydrin therefrom, or may be processed further to convert the dichlorohydrin into derivatives such as epichlorohydrin and/or glycerine.

A disadvantage of the known processes is that substantial amounts of water are used in the reaction zone of the process to reduce formation of undesired by-products, which by-products reduce the overall efficiency of the process, and may complicate purification procedures of the desired product. Such conventional processes after recovery or conversion of the dichlorohydrin result in a substantial volume of an aqueous effluent stream which contains minor amounts of organic impurities. Such effluent requires energy intensive treatment to reduce the amount of organic materials to levels acceptable to be passed to receiving bodies of water such as rivers, lakes and the like. Considerable production cost savings could be effected if the amount of aqueous stream from which the dichlorohydrin is recovered or chemically converted could be significantly reduced. In addition water is an increasingly scarce resource in some locations, and it is highly desirable to be able to reduce the amount of fresh water required to be used in the process, without loss of efficiency. The process according to the invention overcomes such disadvantages.

SUMMARY OF THE INVENTION

According to the invention there is provided a continuous process for the production of dichlorohydrin which comprises:

(a) reacting allyl chloride, water and chlorine in a reaction zone to form an aqueous reaction mixture of dichlorohydrin and reaction by-products, (b) passing said reaction mixture from said reaction zone as feed to a reverse osmosis zone, (c) subjecting said feed to reverse osmosis to afford (1) a retentate stream having a dichlorohydrin content higher than said feed, and (2) a permeate stream having a dichlorohydrin content less than about five per cent by weight of the dichlorohydrin content in said feed, (d) withdrawing said retentate stream, and (e) recycling at least part of said permeate stream to said reaction zone.

THE DRAWING

The drawing depicts a schematic flow of a preferred embodiment of the invention.

DESCRIPTION OF PREFERRED EMBODIMENTS

In the principal reaction, allyl chloride is converted to a mixture of two isomers of glycerol dichlorohydrin by reaction with hypochlorous acid, HClO, which acid is readily formed when chlorine is dissolved in water. Dilute hydrochloric acid, HCl, too is formed when chlorine is dissolved in water. The chlorohydrination reaction takes place readily at temperatures in the range below about 60° C., e.g. in the range from about 15° to about 55° C. For maximum dichlorohydrin yield it is necessary to run the reaction at low concentrations of chloride ion and of dichlorohydrin, i.e., high water dilution reduces the formation of undesired by-products such as e.g., trichloropropane and tetrachloropropyl ether.

The reaction zone effluent typically has a low pH, e.g. in the range below about 1.0 resulting from the above mentioned acids in the reaction mixture. It is preferred that at least a majority of the hydrogen ions in said effluent be neutralized by the addition of a basic substance to facilitate the separation of ionic materials in the subsequent reverse osmosis step and to extend the service life of the reverse osmosis membranes. An additional advantage is that the less corrosive nature of said effluent will permit a wider choice of less expensive materials of construction in the reverse osmosis zone.

The use of excess basic substance is to be avoided to preclude conversion of the dichlorohydrin to epichlorohydrin and the further undesirable side reactions such as hydrolysis and/or hydration of the epichlorohydrin. Upon the addition of the basic substance the pH of said effluent is preferably in the range from about 2.5 to about 6.9; it should not be permitted to exceed about 6.9, and most preferably the pH should be maintained below about 6.6. Although in theory any basic substance can be employed, preference is given to the hydroxides and carbonates of the alkali metals and/or alkaline earth metals. Particularly preferred because of their availability and generally lower cost are caustic soda (sodium hydroxide), lime (calcium hydroxide), and limestone (calcium carbonate).

Optionally, after the neutralization step the reaction effluent may be subjected to a solids removal step to remove any undissolved materials from said effluent so as to minimize fouling of the reverse osmosis membranes. This is particularly desirable when there are substantial amounts of solids present, e.g. when a lime or limestone slurry is used as the basic substance. The solids removal step may comprise any known technique such as sedimentation, centrifugation or filtration. Microporus ultrafiltration is preferred. Any separated solids may be removed from the process, or, if desired, may be recycled to the neutralization step.

The dichlorohydrin content of the reaction zone effluent is concentrated by reverse osmosis, i.e., by applying hydraulic pressure against said effluent and a suitable membrane, said pressure being greater than the osmotic pressure of said effluent. Accordingly said reaction effluent is passed as feed to a reverse osmosis zone and is subjected to reverse osmosis to afford: (1) a retentate stream having a higher dichlorohydrin content than said feed, and a permeate stream having substantially lower content of both organic and inorganic chlorides than said feed. In particular the permeate stream desirably will have a dichlorohydrin content less than about 10% and preferably less than about 5% of the dichlorohydrin content of the reaction zone effluent feed to the reverse osmosis zone.

The reverse osmosis membranes used in the reverse osmosis zone may require some care in selection, since they are required to retain substantially all of the organics in the retentate stream. A conventional polysulfone membrane has been found useful for this purpose, as have thin film composite membranes.

Part, preferably a major portion, and most preferably all of said permeate stream is recycled to the reaction zone. This recycled permeate stream can be used to displace a like amount of the fresh water normally fed to the reaction zone, or if desired can be supplied as additional water to further dilute the reactants thereby enabling greater selectivity to the desired dichlorohydrin product. The amount of the permeate stream which is recycled to the reaction zone may comprise from about 25 to about 90% by volume, and preferably from about 30 to about 80% by volume of the total amount of water fed to the reaction zone.

The retentate stream having both a significantly smaller volume and a higher dichlorohydrin content than the reaction zone effluent is withdrawn and requires significantly less energy for further processing. The retentate stream may comprise from about 10 to about 75% by volume, and preferably from about 20 to about 70% by volume of the volume of the reaction mixture effluent from the reaction zone.

As will be appreciated by those skilled in the art, the present process may be readily applied to an existing process producing dichlorohydrin. The use of lower amounts of fresh water to the process will enable an increase in the production capacity, and may permit a selectivity advantage. Alternatively, one can maintain the production rate and selectivity of the original design, and lower operating costs such as steam requirements and effluent treating costs significantly owing to the reduced amount of fresh water required.

An embodiment of the invention will be described with reference to the figure which shows diagrammatically a preferred assemblage according to the invention. In the figure, a fresh water stream is continuously introduced at a rate of about 330 gallons per minute (gpm) through conduits 10 and 12 and a recycled permeate stream is continuously introduced at a rate of about 670 gpm into reaction zone 14. The reaction zone may comprise one but preferably is two or more reaction stages, e.g. two to about six reaction stages arrayed in series flow. Each reaction stage suitably may be a stirred reactor such as e.g., an agitated vessel or a vane disc disperser; a circulating loop reactor; a sprayed tower or other equipment known to be suitable for chlorohydrination reactions. For simplicity, the reaction zone herein is shown as a single stage.

Referring to the drawing, allyl chloride is continuously fed into reaction zone 14 through conduit 16, while chlorine in an amount substantially equimolar with respect to the allyl chloride is continuously fed to the reaction zone through conduit 18. When the reaction zone comprises a series of reaction stages, a small amount of each of allyl chloride and chlorine are added to the first stage and the relatively dilute first reaction stage effluent is passed to the second stage where further quantities of allyl chloride and chlorine are added resulting in a more concentrated effluent passed to a subsequent stage and so on. Preferably from about 0.02 to 0.1 volume of allyl chloride (and a substantially equimolar quantity of chlorine) is added for each volume of water supplied to the system. When a series a reaction stages is used, it is preferred to add substantially all of the water to the first reaction stage and to let the concentration of dichlorohydrin increase as the additional reactants are added, since this represents the most efficient method of operation.

The reaction may be conducted within a wide temperature range and under atmospheric, subatmospheric or superatmospheric pressures. In general, reaction temperatures between 15° and 60° C., preferably between about 25° and 55° C. can be employed. The reaction between allyl chloride and hypochlorous acid (formed in-situ by the reaction of chlorine and water) proceeds rapidly and is normally complete within one or two seconds; however, total residence time in the reaction zone of from 1 to about 10 minutes may be employed.

Effluent from the reaction zone containing about 0.27 Molar (M) dichlorohydrin and having a temperature of about 57° C. is withdrawn via conduit 20. The reaction zone effluent typically has a low pH, e.g. less than about 1, resulting from the formation of acids in the reaction mixture such as hydrogen chloride by-product in the formation of the dichlorohydrin. It is preferred that at least a majority of the hydrogen ions present in said effluent be neutralized by the addition of a a basic substance e.g. concentrated sodium hydroxide via conduit 22 prior to the reverse osmosis step to facilitate concentration of the ions into the retentate stream, and to reduce and/or prevent chemical degradation of the membranes employed in the reverse osmosis zone. It is preferred that the effluent be partially neutalized to a pH in the range from about 2.5 to about 6.9, and more preferably from about 3.0 to 6.5.

After the neutralization step the reaction effluent is passed via conduit 24 for further processing. Optionally, as shown, this may be a solids removal step in a solids removal zone 26. The solids removal step is to remove any undissolved solids from said effluent so as to minimize fouling of the membranes in the downstream reverse osmosis zone. The solids are removed by e.g. microporous ultrafiltration and separated solids are withdrawn from solids separation zone 26 via conduit 28.

The reaction effluent which will have increased by about 5-10% by volume owing to the addition of the other reactants and the basic material is passed via conduit 30, pump 32 and conduit 34 as feed to reverse osmosis zone 36. The dichlorohydrin content of said effluent is concentrated in said zone by reverse osmosis i.e., by applying hydraulic pressure against said effluent and a suitable membrane, said pressure being greater than the osmotic pressure of said effluent. Said effluent feed is subjected to reverse osmosis to obtain: (1) about 430 gpm of a retentate stream having a dichlorohydrin content of about 0.65 M, and (2) about 670 gpm of a permeate stream of water which is substantially free of dichlorohydrin, i.e. containing about 0.01 M which is about two % of the dichlorohydrin in said feed.

The reverse osmosis membranes used in the reverse osmosis zone may require some care in selection, since they are required to retain substantially all of the organics and most of the inorganics in the retentate stream. A conventional polysulfone membrane has been found useful for this purpose, as have thin film composite membranes.

From reverse osmosis zone 36, part, preferably a majority and most preferably all 670 gpm of said permeate stream is recycled to the reaction zone 14 via conduit 38, optional cooler 40, and conduits 42 and 12. Since both the reaction of formation of the dichlorohydrin and the neutralization reaction are exothermic and the permeate is recycled, optional cooler 40 provides means for cooling said permeate to remove the heat of reaction which would otherwise also be recycled to the reaction zone. Preferably the recycled permeate is cooled to a temperature which is at least 5° C. lower than the temperature of the effluent stream from the reaction zone. Alternatively, the fresh water stream fed to the reaction zone could be cooled via a cooler (not shown). It is also possible to cool the entire reaction zone effluent prior to the reverse osmosis step.

From reverse osmosis zone 36 a retentate stream containing about 0.65 M dichlorohydrin is removed via conduit 44 for further processing and/or conversion into derivatives.

We claim:

1. A continuous process for the production of dichlorohydrin which comprises:
    (a) reacting allyl chloride, water and chlorine in a reaction zone to form an aqueous reaction mixture of dichlorohydrin and reaction by-products,
    (b) passing said reaction mixture from said reaction zone as feed to a reverse osmosis zone,
    (c) subjecting said feed to reverse osmosis to afford: (1) a retentate stream having a dichlorohydrin content higher than said feed, and (2) a permeate stream having a dichlorohydrin content less than about 10 per cent of the dichlorohydrin content in said feed,
    (d) withdrawing said retentate stream, and
    (e) recycling at least part of said permeate stream to said reaction zone in an amount from about 25 to about 90% by volume of the volume of the total amount of water fed to said reaction zone.

2. A process as in claim 1 wherein said permeate stream recycled to said reaction zone is cooled to a temperature at least about 5° C. lower than the temperature of the effluent stream from the reaction zone.

3. A process as in claim 1 wherein the volume of retentate stream comprises from about 30 to about 80% of the volume of the reaction mixture effluent from the reaction zone.

4. A process as in claim 1 wherein intermediate to steps (a) and (b), a basic substance is added to the reaction mixture to neutralize at least a majority of the hydrogen ions present in said reaction mixture.

5. A process as in claim 4 wherein the neutralized reaction mixture which is passed to the reverse osmosis zone has a pH in the range from about 2.5 to about 6.9.

* * * * *